United States Patent
Norita et al.

(10) Patent No.: US 6,788,807 B1
(45) Date of Patent: Sep. 7, 2004

(54) THREE DIMENSIONAL INFORMATION MEASUREMENT METHOD AND APPARATUS

(75) Inventors: Toshio Norita, Osaka (JP); Takashi Kondo, Sakai (JP); Eiro Fujii, Takatsuki (JP); Fumiya Yagi, Toyonaka (JP)

(73) Assignee: Minolta Co., Ltd., Osaka (JP)

( * ) Notice: Subject to any disclaimer, the term of this patent is extended or adjusted under 35 U.S.C. 154(b) by 700 days.

(21) Appl. No.: 09/243,794

(22) Filed: Feb. 3, 1999

Related U.S. Application Data

(60) Provisional application No. 60/101,648, filed on Sep. 23, 1998.

(30) Foreign Application Priority Data

Feb. 13, 1998 (JP) .......................................... 10-030825

(51) Int. Cl.[7] ................................................ G06K 9/00
(52) U.S. Cl. ...................... 382/154; 250/230; 250/234; 356/608; 356/613; 359/216; 359/874; 359/876; 382/103; 382/203
(58) Field of Search ................................ 382/154, 203; 359/385, 216; 250/559.22, 474.1, 221, 222.7, 234, 235, 236

(56) References Cited

U.S. PATENT DOCUMENTS

| | | | | |
|---|---|---|---|---|
| 5,461,478 A | * | 10/1995 | Sakakibara et al. .......... | 356/623 |
| 5,606,174 A | * | 2/1997 | Yoshimura et al. .... | 250/559.22 |
| 5,668,631 A | | 9/1997 | Norita et al. | |
| 5,694,235 A | * | 12/1997 | Kajiki ......................... | 359/202 |
| 5,780,866 A | * | 7/1998 | Yamamura et al. .... | 250/559.22 |
| 5,801,812 A | * | 9/1998 | Lo et al. ........................ | 355/22 |
| 5,848,188 A | * | 12/1998 | Shibata et al. .............. | 382/203 |
| 5,870,220 A | * | 2/1999 | Migdal ........................ | 359/216 |
| 5,936,764 A | * | 8/1999 | Kobayashi ................... | 359/385 |
| 6,044,170 A | * | 3/2000 | Migdal et al. .............. | 382/154 |
| 6,218,673 B1 | * | 4/2001 | Gore et al. .............. | 250/474.1 |

FOREIGN PATENT DOCUMENTS

| | | |
|---|---|---|
| JP | 3-138508 | 6/1991 |
| JP | 5-223547 | 8/1993 |
| JP | 5-322526 | 12/1993 |
| JP | 7-174536 | 7/1995 |
| JP | 7-191142 | 7/1995 |
| JP | 7-299921 | 11/1995 |
| JP | 8-308106 | 11/1996 |

* cited by examiner

*Primary Examiner*—Bhavesh M. Mehta
*Assistant Examiner*—Gregory Desire
(74) *Attorney, Agent, or Firm*—Burns, Doane, Swecker & Mathis, L.L.P.

(57) ABSTRACT

Method and apparatus for measuring three dimensional information of a target placed in an interior space of a rotator type mirror by using the rotator type mirror in combination with an imaging apparatus disposed with its light receiving axis aligned with a center axis of the rotator type mirror. The invention includes projecting reference light toward the rotator type mirror from a position on the center axis, and scanning the target with mirror reflected reference light that is produced by reflecting the reference light on the rotator type mirror. The invention further includes obtaining the three dimensional information of the target, based on a physical quantity corresponding to the projection angle of the reference light and on a physical quantity corresponding to the position of a projected image obtained when the mirror reflected reference light that scanned the target is captured by the imaging apparatus via the rotator type mirror.

24 Claims, 7 Drawing Sheets

US 6,788,807 B1

THREE DIMENSIONAL INFORMATION MEASUREMENT METHOD AND APPARATUS

Priority is claimed to Japanese Application No. 10-030825 filed on Feb. 13, 1998 and to U.S. Provisional Application No. 60/101,648 filed on Sep. 23, 1998, both of which are herein incorporated by reference.

BACKGROUND OF THE INVENTION

1. Technical Field of the Invention

The present invention relates to a three dimensional information measurement method and apparatus for measuring three dimensional information on a target such as an object or a human body around the entire circumference thereof or from multiple viewpoints (multiple directions), and for inputting the measured information.

2. Description of Related Art

In the medical, apparel, or like fields, measuring three dimensional information of a target such as a human body or an object around the entire circumference thereof has been practiced for many years.

In the prior art, the following three dimensional information measurement methods have been proposed.

(1) While holding a target stationary, a distance measurement apparatus, constructed by combining a projection system and a light receiving system in one unit, is moved (turned) in a circle centered about the target with the line of sight of the apparatus being constantly directed to the object. Based on the distance information thus obtained around the entire circumference of the object, the three dimensional information of the target is computed (see, Japanese Patent Unexamined Publication No. 5-223547).

(2) While holding the distance measurement apparatus stationary, the target is moved, and its three dimensional information is computed in a manner similar to the above (see, Japanese Patent Unexamined Publication No. 5-322526). The object is placed, for example, on a rotating stage. Reference light is projected from the projection system of the distance measurement apparatus onto the target, and its reflected light is captured via a plurality of mirrors into a television camera which is the light receiving system. The distance information of the object is thus obtained around the entire circumference thereof, and based on this information, the three dimensional information is computed.

(3) There is also a method in which neither the distance measurement apparatus nor the target is rotated. In this method, distance measurement apparatuses, each constructed with a projection system paired with a light receiving system, are arranged at several locations around the target, and the distance information of the target is captured by the respective distance measurement apparatuses in a one-shot operation. Based on this distance information, the three dimensional information of the target is computed (see, Japanese Patent Unexamined Publication No. 3-138508).

However, according to the first method (1), the mechanism for moving the distance measurement apparatus becomes complex. Further, because of the necessity to stabilize apparatus operation and ensure safety, the moving speed of the distance measurement apparatus cannot be increased sufficiently. This lengthens the time required for measuring. Accordingly, when a target is a living creature such as a human being or an animal, making measurements is extremely difficult as the target tends to move during measuring.

In the second method (2) also, there are problems similar to those of the first method (1); that is, the mechanism for rotating the stage tends to increase in size and complexity, and further, the time required for measuring becomes long.

In the third method (3), the feature of being able to obtain the distance information around the entire circumference of a target in a one-shot operation solves the problems of increased complexity of the rotating mechanism and increased measuring time associated with the first two methods (1) and (2), but the need for a plurality of distance measurement apparatuses increases the cost. Further, because of the use of the plurality of distance measurement apparatuses, processing for image merging becomes necessary to integrate the three dimensional information obtained by the respective light receiving systems; this increases the complexity of processing.

OBJECTS AND SUMMARY OF THE INVENTION

The present invention has been devised in view of the above problems, and an object of the invention is to provide a three dimensional information measurement method and apparatus for measuring three dimensional information on a target around the entire circumference thereof or from multiple viewpoints at high speed using a relatively simple configuration, and for inputting the measured information.

According to one aspect of the invention, there is provide a three dimensional information measurement method for measuring three dimensional information on a target placed in an interior space of a rotator type mirror by using the rotator type mirror in combination with an imaging apparatus disposed with its light receiving axis aligned with a center axis of the rotator type mirror, comprising: projecting reference light toward the rotator type mirror from a position on the center axis, and scanning the target with mirror reflected reference light that is produced by reflecting the reference light on the rotator type mirror; and obtaining the three dimensional information of the target, based on a physical quantity corresponding to the projection angle of the reference light and on a physical quantity corresponding to the position of a projected image obtained when the mirror reflected reference light that scanned the target is captured by the imaging apparatus via the rotator type mirror.

According to another aspect of the invention, there is provided a three dimensional information measurement apparatus for measuring three dimensional information on a target placed in an interior space of a rotator type mirror by using the rotator type mirror in combination with an imaging apparatus disposed with its light receiving axis aligned with a center axis of the rotator type mirror, comprising: reference light projection means for projecting reference light toward the rotator type mirror from a position on the center axis; main scanning means for deflecting the reference light so that mirror reflected reference light, produced by reflecting the reference light on the rotator type mirror, scans the target around the circumference thereof; sub scanning means for deflecting the projection angle of the reference light so that the mirror reflected reference light scans the target in a direction parallel to the center axis; and three dimensional information computing means for obtaining the three dimensional information of the target, based on a physical quantity corresponding to the projection angle of the reference light and on a physical quantity corresponding to the position of a projected image obtained when the mirror reflected reference light that scanned the target is captured by the imaging apparatus via the rotator type mirror.

For the physical quantity corresponding to the projection angle, the projection angle itself or the physical quantity associated with the projection angle is used, such as the elapsed time from the start of the sub scan or the amount of movement of a moving mechanism used to deflect the projection angle. For the physical quantity corresponding to the position of the projected image, the distance of the position of the projected image from a reference position, the coordinates of the pixel on which the projected image is projected, or the direction opposing the pixel on which the projected image is projected, is used.

In this specification, the term "on the center axis" includes points on the center axis and its surroundings.

The "rotator type mirror" used in this specification means a mirror surface or its equivalent in a shape formed by rotating a line or quadratic curve such as a parabola, hyperbola or ellipse around a generatrix or axis and includes, for example, a combination of a large number of narrow rectangular plane mirrors arranged to approximate the shape of the rotator.

According to the present invention, three dimensional information of a target can be measured for input at high speed from around the entire circumference thereof or from multiple viewpoints by using a relatively simple configuration.

BRIEF DESCRIPTION OF THE DRAWINGS

The present invention will now be described by way of exemplary embodiments to which it is not limited illustrated in the accompanying drawings in which.

DETAILED DESCRIPTION OF PREFERRED EMBODIMENTS

Figure 1:
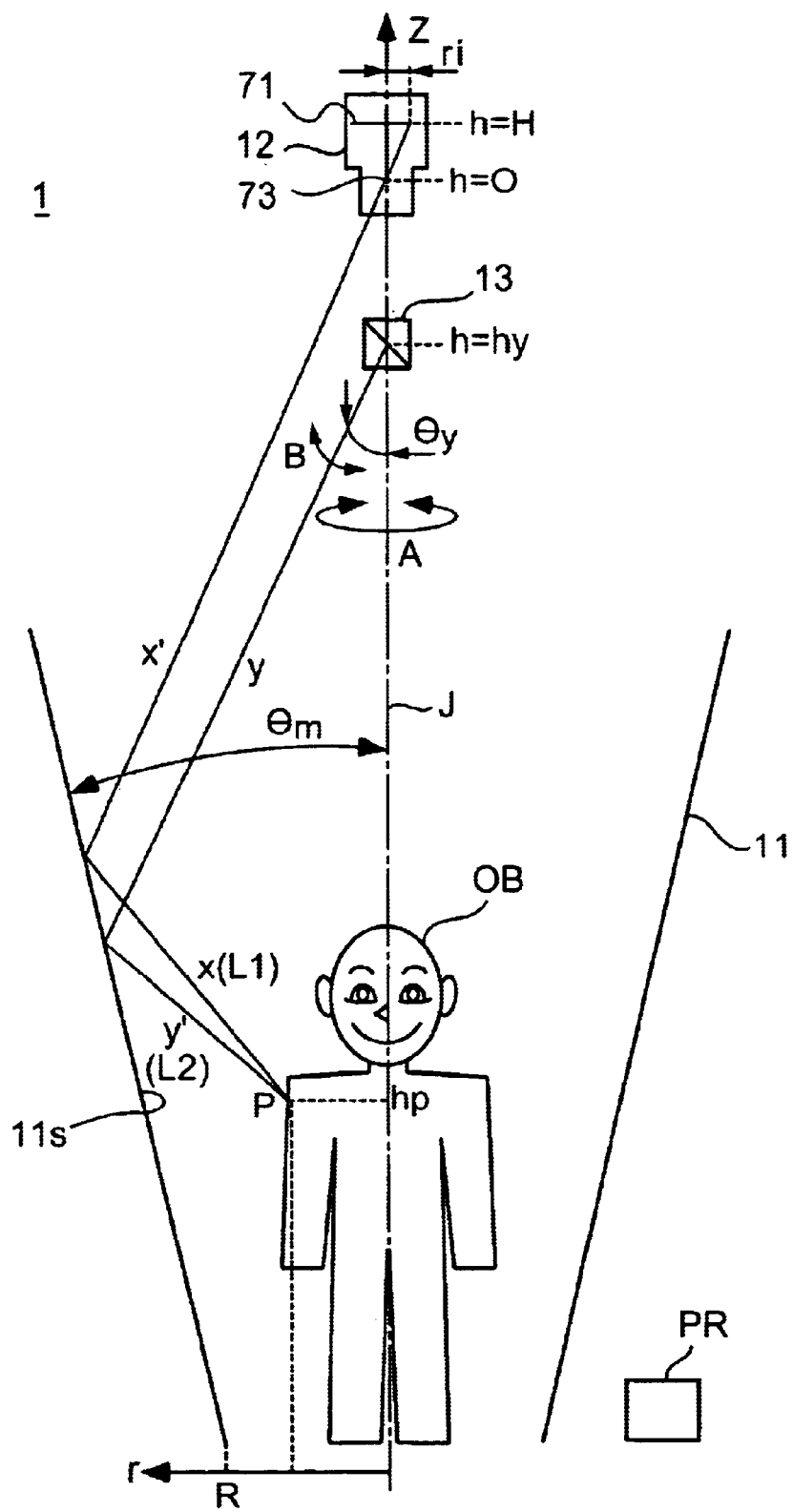
FIG. 1 is a diagram showing the configuration of a three dimensional information measurement apparatus according to the present invention.

FIG. 1 is a diagram showing the configuration of a three dimensional information measurement apparatus 1 according to the present invention.

In FIG. 1, the three dimensional information measurement apparatus 1 includes an imaging mirror 11, an imaging apparatus 12, and a reference light projection apparatus 13.

The imaging mirror 11 is a rotator type mirror (or a rotated-surface type mirror) in the shape of an inverted truncated cone with a hollow interior and with its inner circumferential surface formed as a reflecting surface 11S.

That is, the imaging mirror 11 is placed with its center axis J arranged along the vertical direction and with the larger base of the truncated cone facing up. Because of this shape of the imaging mirror 11, when an object OB is placed inside the imaging mirror 11, images of the entire circumference of the object OB are reflected in the reflecting surface 11S.

Upward of the imaging mirror 11 is arranged the imaging apparatus 12 in such a manner that its light receiving axis coincides with the axis J. The imaging apparatus 12 includes an optical lens and an imaging device 71. A video camera, for example, is used as the imaging apparatus 12. Since light reflected by the entire circumference of the imaging mirror 11 is introduced into the imaging apparatus 12, images of the entire circumference of the object OB, that is, the object OB seen from all directions, can be captured by the imaging apparatus 12. Accordingly, images of the object OB seen from all viewpoints around the axis J, except those near the top of the object OB, are simultaneously taken into a single image when captured by the imaging device 71 in the imaging apparatus 12.

Disposed below the imaging apparatus 12 and along the axis J is the reference light projection apparatus 13.

The shape, size, disposition, etc. of the reference light projection apparatus 13 are determined so as not to interfere with the light reception by the imaging apparatus 12. More specifically, the reference light projection apparatus 13 is arranged so as to be positioned within a cylindrical region near the center of the field of view of the imaging apparatus 12, where the reflecting surface 11S of the imaging mirror 11 does not exist when seen from the imaging apparatus 12, and where no interference is caused to the inputting of the three dimensional information.

The reference light projection apparatus 13 projects a reference light beam toward the imaging mirror 11. The reference light projection apparatus 13 is constructed so that the projecting direction of the reference light beam can be deflected about the axis J of the imaging mirror 11 in such a manner as to circle outwardly around the circumference thereof, as shown by arrow A in FIG. 1, and so that the projection angle θy of the reference light beam can be deflected within a vertical plane, as shown by arrow B in FIG. 1. The deflection in the circumferential direction is accomplished by rotating the whole or part of the reference light projection apparatus 13 by means of a motor or a driving device using a motor, gear, etc. The deflection in the vertical direction can be easily accomplished using a scanning device such as a galvanometer scanner.

The reference light beam projected from the reference light projection apparatus 13 is reflected by the imaging mirror 11. The object OB is scanned around the entire circumference thereof and also in the direction parallel to the axis J by the reflected reference light beam. The reflected reference light beam corresponds to the mirror reflected reference light in the present invention. In this specification, the scan in the circumferential direction about the axis J is the main scan, and the scan in the direction parallel to the axis J is the sub scan.

In the three dimensional information measurement apparatus 1, the object OB is scanned from all directions by combining the main scan and the sub scan, and computation of the three dimensional information is performed by a three dimensional information computing section PR which is described later.

A description will now be given of the principle on how images of the entire circumference of the object OB are reflected in the imaging mirror 11 and captured by the imaging apparatus 12.

Figure 2:
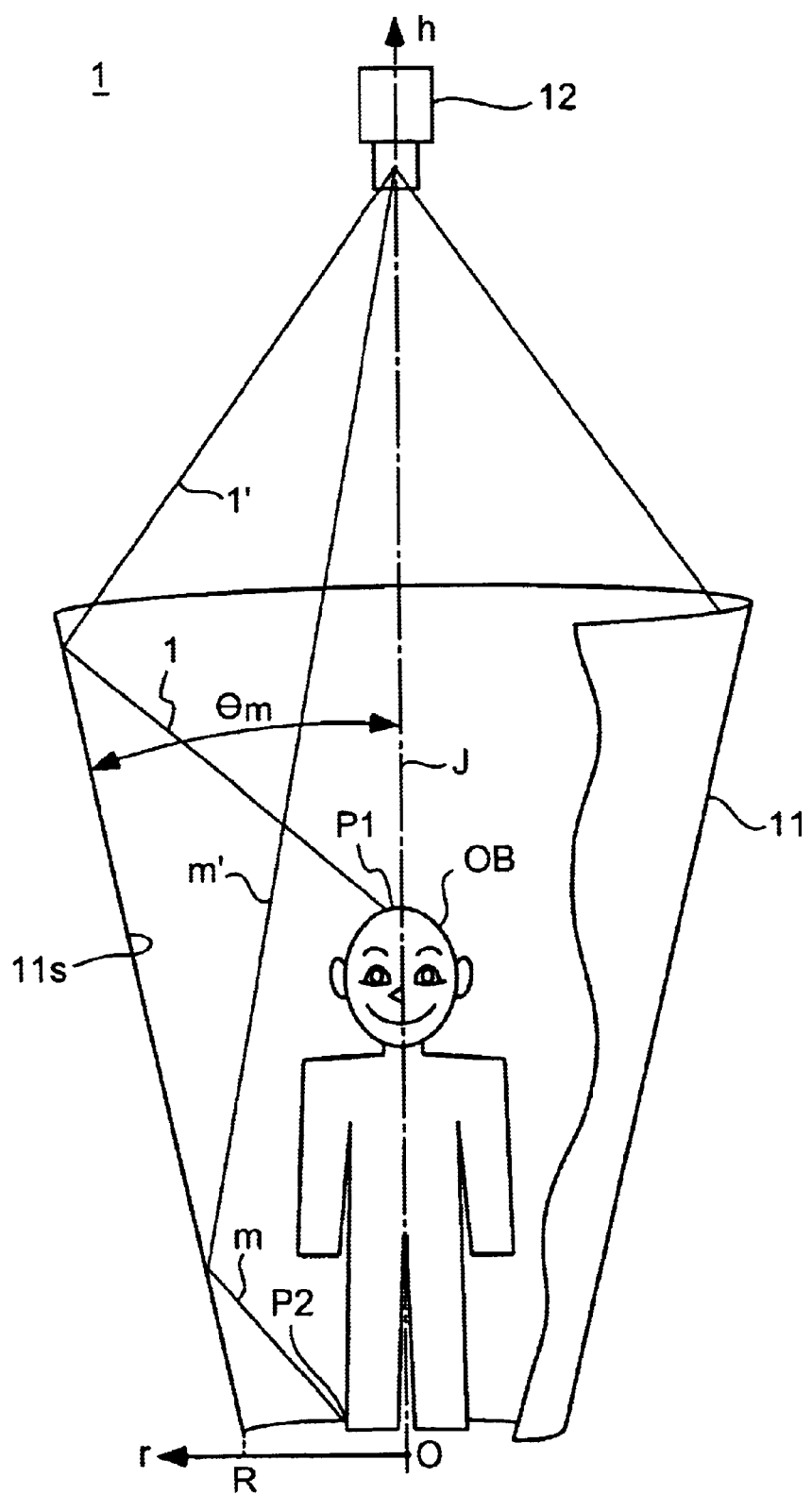
FIG. 2 is a diagram for explaining the principle on how images of the entire circumference of an object are captured by an imaging apparatus.
Figure 3:
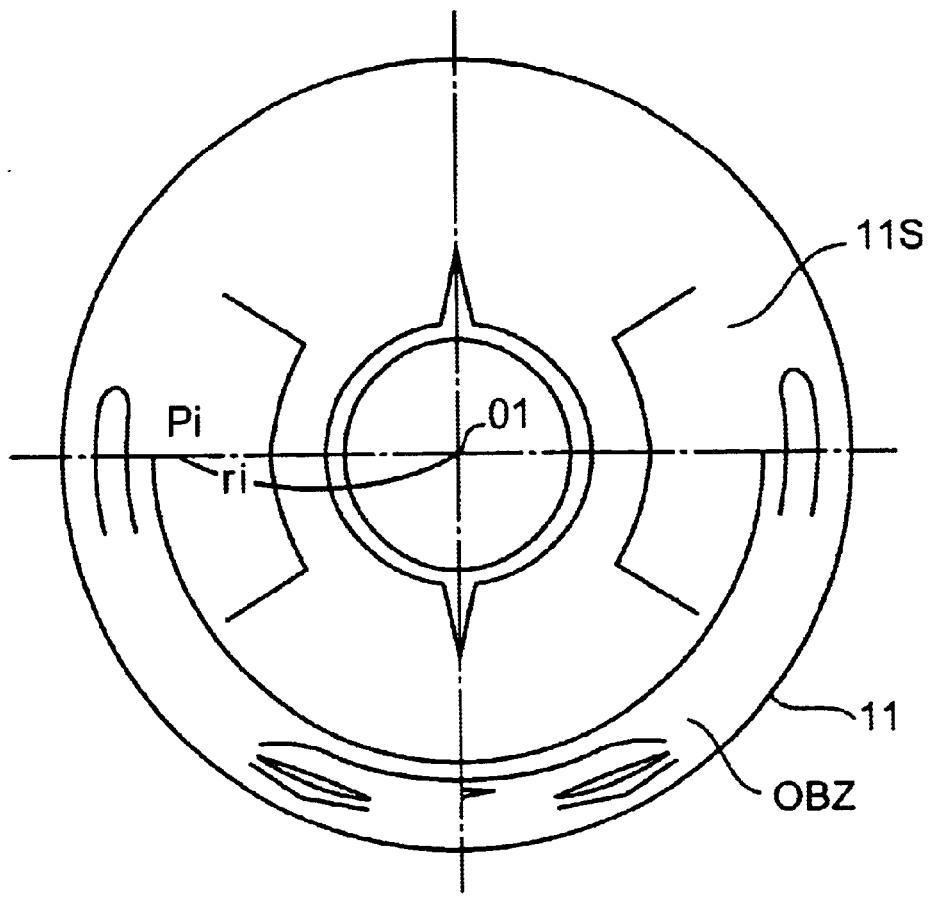
FIG. 3 is a diagram showing an example of an image of the object reflected in an imaging mirror.

FIG. 2 is a diagram for explaining the principle on how images of the entire circumference of the object OB are captured by the imaging apparatus 12, and FIG. 3 is a diagram showing the imaging mirror 11 photographed by the imaging apparatus 12 and the image of the object OB reflected in the imaging mirror 11.

In a coordinate system with its origin taken at O, h axis along the vertical direction, and r axis along a radial direction, as shown in FIG. 2, the shape of the imaging mirror 11 is expressed by the following equation (1).

$$r = h \cdot \tan \theta m + R \quad (1)$$

where R is the radius of the geometrical base of the imaging mirror 11, and θm is the angle that the vertical axis makes with the generator of the imaging mirror 11, i.e., the reflecting surface 11S.

Here, the angle θm, the distance between the imaging mirror 11 and the imaging apparatus 12, the angle of view of the imaging apparatus 12, etc. are respectively set so that images of the entire circumference of the object OB can be captured by the imaging apparatus 12 when the object OB is placed inside the imaging mirror 11.

For example, images of points P1 and P2 on the object OB are captured by the imaging apparatus 12 via paths 1 and 1' and paths m and m', respectively. By applying this concept to all the points on the object OB, the images of the entire circumference of the object OB are captured by the imaging apparatus 12.

In FIG. 3, an image OBZ is the image of the object OB reflected in the reflecting surface 11S. Point Pi on the image OBZ corresponds to point P on the object OB in FIG. 1.

Description of Method for Three Dimensional Information Computation

Next, a description will be given of how the three dimensional information is computed in the three dimensional information computing section PR. First, the principle of the three dimensional information computation will be described.

In FIG. 1, the reference light beam projected at a projection angle of θy from the reference light projection apparatus 13 is directed through a path y to the imaging mirror 11 which reflects the beam through a path y' onto the object OB. Then, it is reflected by the object OB and enters the imaging apparatus 12 via paths x and x'.

It is assumed here that an image of the point P on the object OB in FIG. 1 is observed as the point Pi located at a distance (image height) ri from the center O1 of the image OBZ in FIG. 3. Since the three dimensional information measurement apparatus 1 is symmetrical about the axis J, for simplicity the following description assumes that the angular position in the circumferential direction is fixed, and considers a given vertical plane containing the axis J. At this time, the point P lies on the straight line L1 expressed by the following equation (2) using the distance ri.

$$r = h \cdot \tan\{a \tan(ri/H) + 2\theta m\} + R[H \cdot \tan\{a \tan(ri/H) + 2\theta m\} + ri]/(H \cdot \tan \theta m + ri)$$

Here, the assumption is that the principal point position 73 of the lens system in the imaging apparatus 12 is at h=0 and the position of the imaging device 71 is at h=H.

On the other hand, it is assumed that at a given timing the reference light beam is incident on the point P via the paths y and y'. Here, the projection originating point of the reference light beam, that is, the reference light projection apparatus 13, is assumed to be located at position h=hy. At a certain projection angle θy, the reference light beam is incident on the reflecting surface 11S via the path y and, after reflection, travels along the path y' expressed by the following equation (3). That is, the point P lies on the straight line L2 describing the path y'.

$$r = h \cdot \tan(\theta y + 2\theta m) + \{\tan \theta y (hy \cdot \tan \theta m + R) - \tan(\theta y + 2\theta m)(hy \cdot \tan \theta y - R)\}/(\tan \theta m + \tan \theta y) \quad (3)$$

From the above, the position of the point P is found as the intersection of the paths x and y', that is, the intersection of the straight lines L1 and L2. Therefore, the position of the point P can be computed from the distance ri and the projection angle θy of the reference light beam.

The imaging apparatus 12 uses an imaging device such as a CCD for converting an image into an electrical signal. Many of the imaging devices currently commercialized are constructed with a large number of light sensitive elements arranged in a Cartesian coordinate system.

The position of the point P can therefore be found by knowing the projection timing of the reference light beam continuously scanning with changing projection angle θy, that has contributed to the formation of an image focused as point Pi on the pixel of the imaging device 71. That is, by controlling the reference light projection apparatus 13 by a prescribed means, the elapsed time from the scan start can be associated with the projection angle θy of the reference light beam. On the other hand, the distance ri can be found from the coordinates of the point Pi by predefining the coordinates of the pixel on the imaging device 71 located at the position corresponding to the optical axis.

By repeating the above processing during one revolution in the direction of arrow A in FIG. 1, that is, by repeating the processing of finding the straight lines L1 and L2 based on the distance ri and projection angle θy and computing the position of the point P from their intersection, the contour of the object OB cut by a horizontal plane can be obtained. Further, by repeating this processing for each sub scan being moved in the direction of arrow B parallel to the axis J in FIG. 1, the contours are stacked one on top of another in the vertical direction, and thus the three dimensional shape information around the entire circumference of the object OB and in the direction parallel to the axis J can be acquired.

When attention is paid to the output of a given pixel on the imaging device 71 while capturing images of the reference light beam by the imaging apparatus 12, the output of the pixel shows a maximum value at the instant that the reference light beam passes the point on the object OB which is focused on that pixel. Therefore, for each pixel, processing should be performed to record the timing at which its output shows a peak.

Next, a description will be given of a specific circuit for performing the processing to record the timing at which the reference light beam is shone onto a given pixel on the imaging device 71 by associating the timing with that pixel, and for detecting the output peak information.

Figure 4:
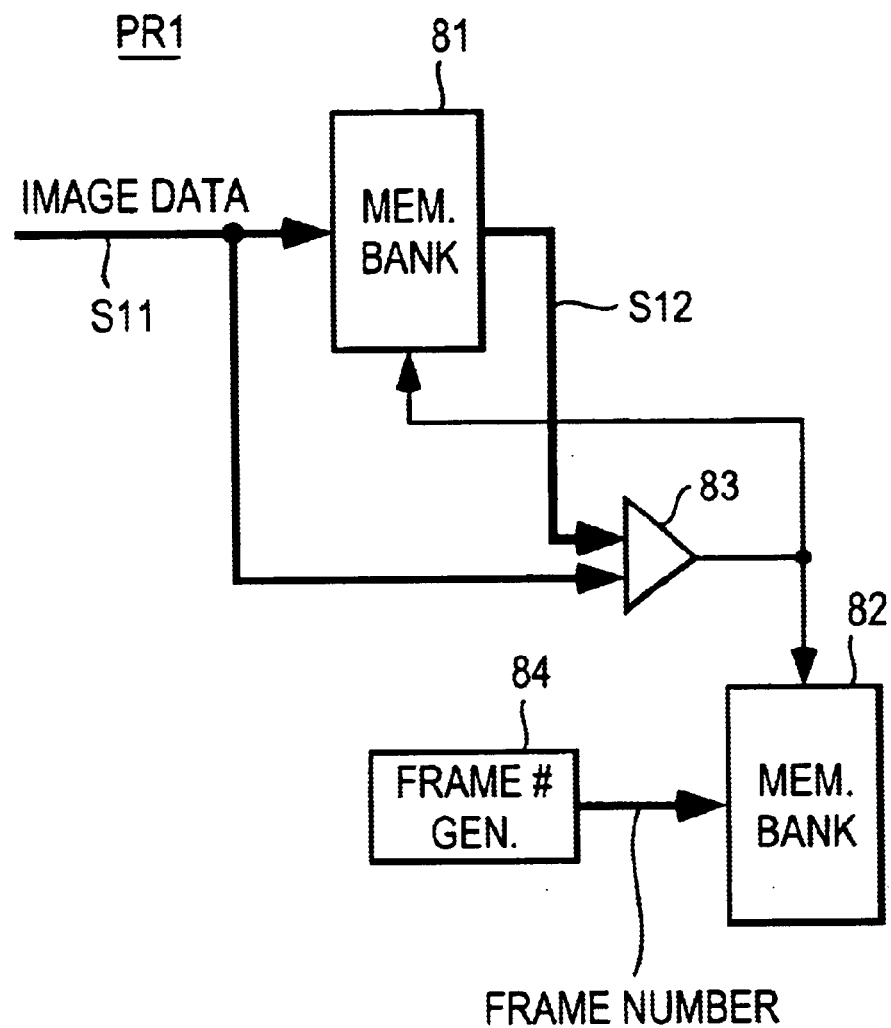
FIG. 4 is a block diagram showing an example of a processing circuit for the three dimensional information measurement apparatus.
Figure 5:
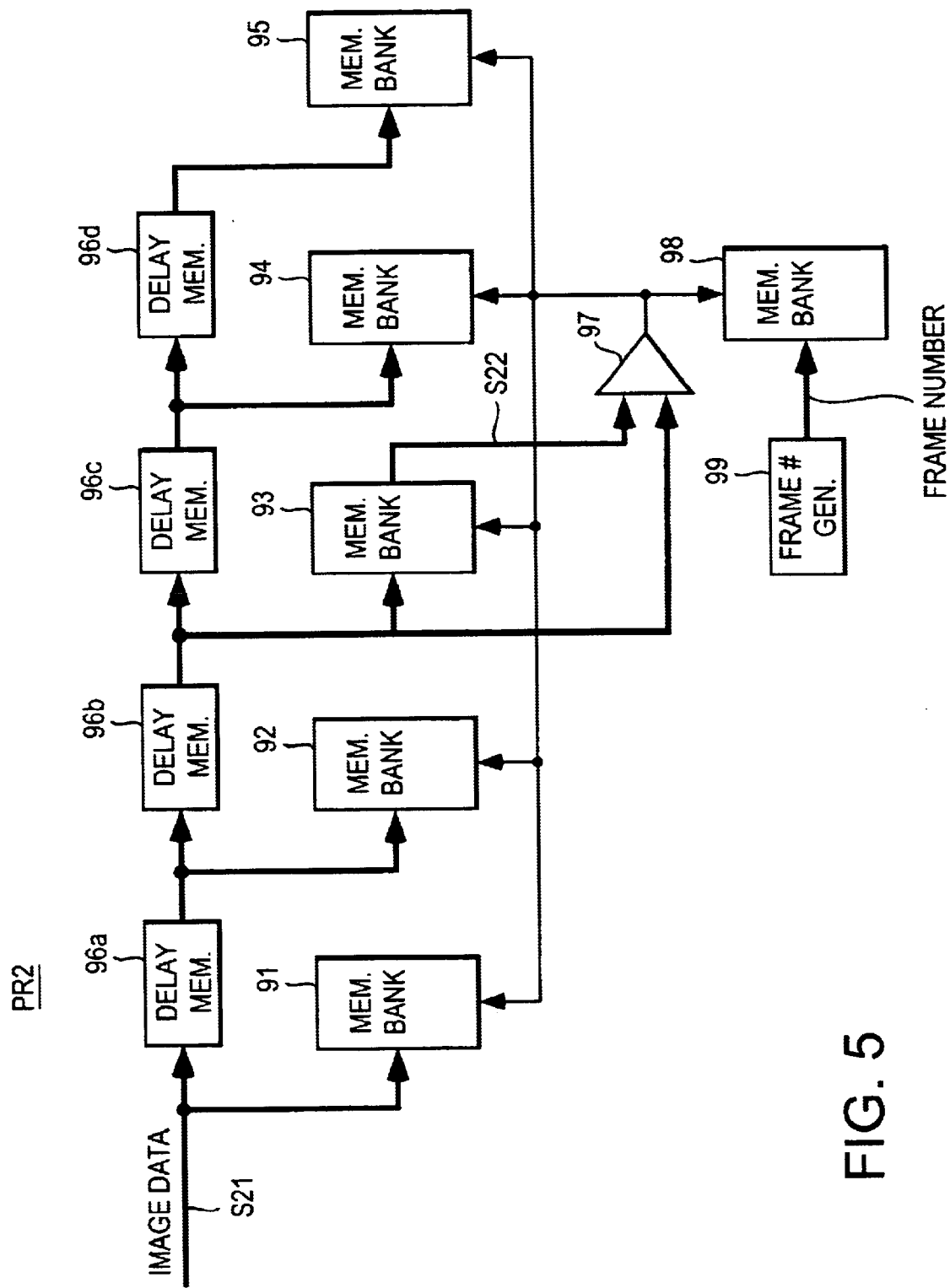
FIG. 5 is a block diagram showing another example of the processing circuit for the three dimensional information measurement apparatus.
Figure 6:
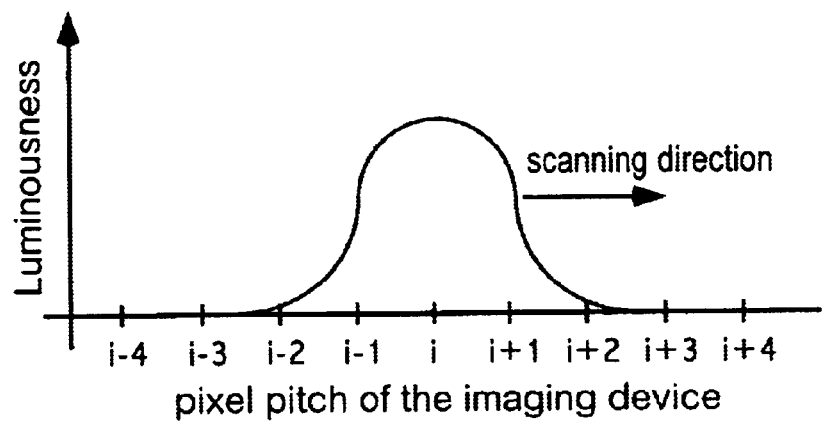
FIG. 6 is a diagram showing an example of the thickness and luminance of projected light on an imaging device.
Figure 7:
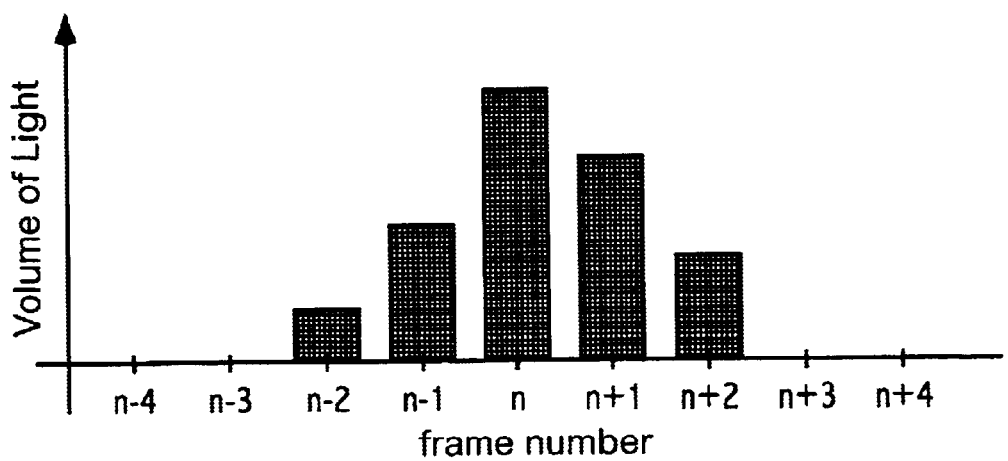
FIG. 7 is a diagram showing the changing amount of light for one pixel on the imaging device.
Figure 8:
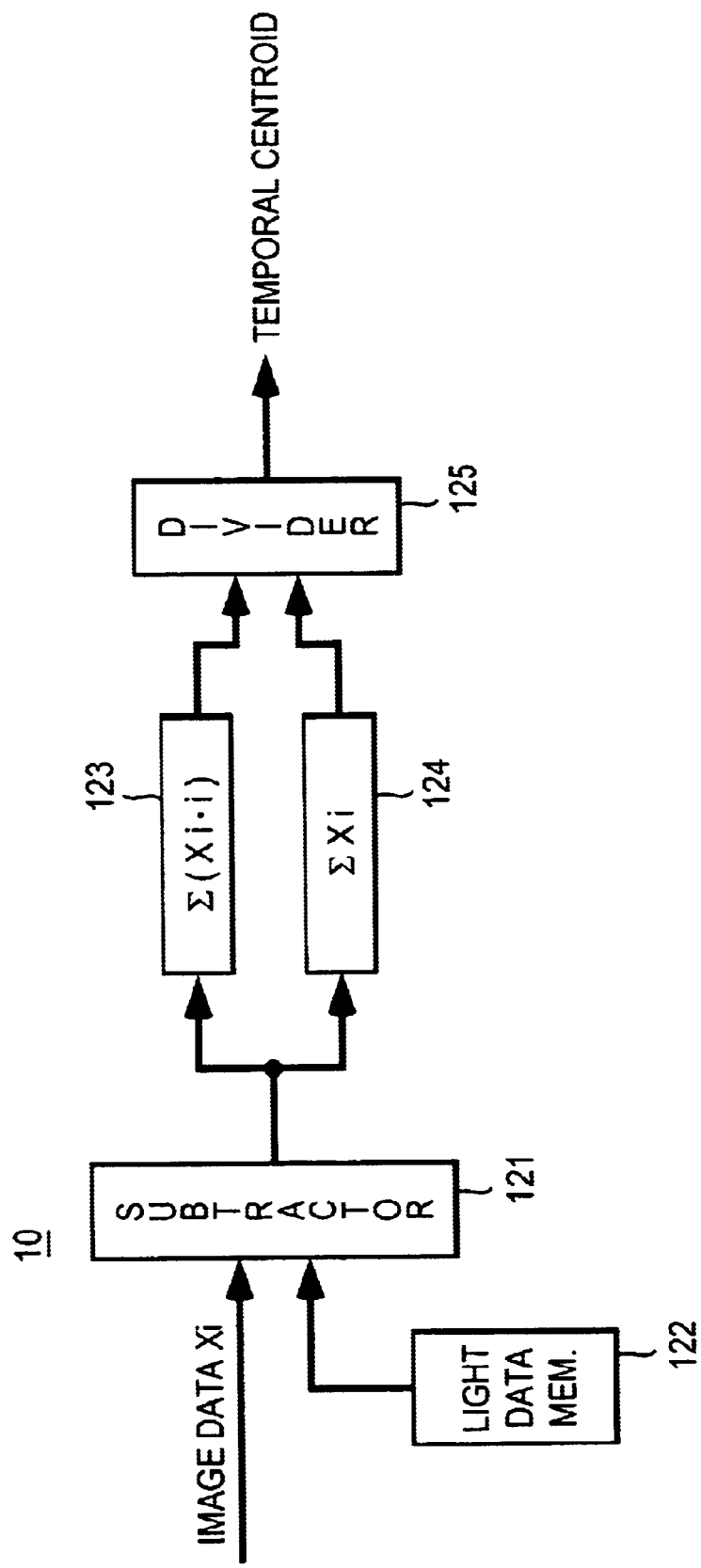
FIG. 8 is a block diagram showing the configuration of a processing circuit for computing the temporal centroid of image data.

FIG. 4 is a block diagram showing an example of the processing circuit (three dimensional information computing section) in the three dimensional information measurement apparatus 1, FIG. 5 is a block diagram showing another example of the processing circuit in the three dimensional information measurement apparatus 1, FIG. 6 is a diagram showing an example of the thickness and luminance of the projected light (reference light beam) on the imaging device 71, FIG. 7 is a diagram plotting the changing amount of light from frame to frame, of the projected light when attention is paid to one particular pixel on the imaging device 71, and FIG. 8 is a block diagram showing the configuration of a processing circuit 10 for computing the temporal centroid of image data.

In FIG. 4, thick arrows indicate primarily data flow, and thin arrows indicate primarily command flow. This also applies in FIG. 5.

As shown in FIG. 4, the processing circuit PR1 consists of two memory banks 81 and 82, a comparator 83, and a frame number generator 84. The memory banks 81 and 82 each have a storage capacity equivalent to the data size of the image obtained by the imaging apparatus 12.

Analog image data output from the imaging device 71 is converted by a known analog processing circuit into digital image data, which is then input to the processing circuit PR1.

Of the image data of each pixel, the luminance value of the pixel is written into the memory bank 81. The image frame number at the time that the luminance shows a peak value for each pixel of the imaging device 71 is written into the other memory bank 82. The image frame number corresponds to the time that elapsed from the time that the above process for inputting the three dimensional information was started. Therefore, if one revolution of the reference light beam scanning in the direction of arrow A at a given projection angle θy in the direction of arrow B in FIG. 1 is made to correspond with one frame, then the elapsed time corresponds to the projection angle θy of the reference light beam scanning in the direction of arrow B. That is, the image frame number corresponds to the projection angle θy of the projected light when scanning the object OB in the sub scan direction.

The luminance value S11 in the image data input to the processing circuit PR1 is compared by the comparator 83 with the luminance value S12 of the same pixel in the memory bank 81 where the largest luminance value of the past is stored for each pixel. If the input luminance value S11 is larger than the luminance value S12 stored in the memory bank 81, the luminance value at the address in the memory bank 81 corresponding to that pixel is updated with the luminance value S11, and also, the contents at the corresponding address in the memory bank 82 is updated with the frame number supplied from the frame number generator 84.

By repeating the above process the number of times equal to the total number of frames which is determined by the number of pixel rows on the imaging device 71 and other conditions, the luminance value at the time that the output of each pixel showed a peak value is stored in the memory bank 81, and the corresponding frame number is stored in the memory bank 82. Based on the frame number stored in the memory bank 82, the projection angle θy of the projected light at the time the luminance shows a peak value is obtained for each pixel.

In each frame, for the projection angle of the reference light beam in the direction of arrow A in FIG. 1, the azimuth angle of each pixel relative to the optical axis can be directly applied.

According to the processing circuit PR1, the projection angle θy (or its corresponding physical quantity) of the projected light (reference light beam) can be obtained using relatively simple circuitry. However, in the processing circuit PR1, the resolution of the projection angle θy cannot be made higher than the pixel pitch of the imaging device 71.

Referring now to FIG. 5, a processing circuit PR2 will be described wherein the circuit configuration of the processing circuit PR1 is extended so as to achieve higher resolution in obtaining the projection angle θy.

As shown in FIG. 5, the processing circuit PR2 consists of delay memories 96a, 96b, 96c, and 96d, bank memories 91, 92, 93, 94, 95, and 98, a comparator 97, and a frame number generator 99. Each of the memory banks 91 to 95 and 98 has a storage capacity equivalent to the data size of the image obtained by the imaging apparatus 12. Each of the delay memories 96a to 96d delays input image data by one frame.

The delay memories 96a to 96d are connected in series, and signals output from the delay memories 96a to 96d are latched into the memory banks 92 to 95, respectively. This makes it possible to simultaneously reference the image data of five successive frames.

The luminance value S21 in the image data input to the processing circuit PR2 is compared by the comparator 97, after being delayed by two frames, with the luminance value S22 of the same pixel in the memory bank 93 where the largest output value of the past is stored for that pixel. If the luminance value S21 in the image data delayed by two frames is larger than the luminance value of the same pixel stored in the memory bank 93, the luminance values input to the respective memory banks 91 to 95 at that time are written to update the luminance values stored at the corresponding addresses in the memory banks 91 to 95. Further, the contents at the corresponding address in the memory bank 98 are updated with the frame number of the output data supplied from the frame number generator 99.

By repeating the above processing until completion of the scanning by the reference light beam, the following contents are stored in the memory banks 91 to 95 and 98. That is, the luminance value at the time each pixel showed a peak value is stored in the memory bank 93, the luminance value of the same pixel due to the projected light one frame after the pixel showed the peak value is stored in the memory bank 92, and the luminance value of the same pixel due to the projected light two frames after the pixel showed the peak value is stored in the memory bank 91. On the other hand, the luminance value of the same pixel due to the projected light one frame before the pixel showed the peak value is stored in the memory bank 94, and the luminance value of the same pixel due to the projected light two frames before the pixel showed the peak value is stored in the memory bank 95. Their corresponding frame numbers are stored in the memory bank 98.

It is assumed here that the projected light has a thickness equivalent to five pixels when focused on the imaging device 71, and that its luminance distribution is a monotonic bell-shaped curve having one peak value at the center, like a Gaussian distribution, as shown for example in FIG. 6. In this case, when attention is paid to one particular pixel and the change in the amount of projected light is plotted frame by frame, then the graph shown in FIG. 7 is obtained.

That is, the amount of light incident on the particular pixel exhibits significant values for five frames, and the value changes from one frame to the next. Further, the value changes in a monotonically increasing and monotonically decreasing manner like a Gaussian distribution. Accordingly, after the series of processing, the data stored in the memory banks 91 to 95 are such that the amount of light increases in the order of the memory bank 95 and the memory bank 94, reaching a maximum in the memory bank 93, and decreases in the order of the memory bank 92 and the memory bank 91. By calculating the centroid based on the data stored in the five memory banks 91 to 95, the center point of the projected light, that is, the position of the peak value, can be obtained with resolution higher than the frame spacing or pixel pitch. An algorithm for such centroid computation is described in detail in Japanese Patent Unexamined Publication No. 7-299921 disclosed by applicant.

As described above, according to the processing circuit PR2, the projection angle θy of the projected light can be obtained with higher resolution than the pixel pitch of the imaging device 71 and, therefore, the three dimensional information can be measured with higher accuracy. In reality, however, some form of noise is often introduced in the image of the projected light because of the characteristics of optics at the projection side and the imaging apparatus 12. This may result in the occurrence of a plurality of peak values in the luminance distribution, or in the distribution tending to become flat and blurring the position of the peak value, deviating widely from the ideal shape. In such cases, with the above method, the calculation result of the peak value position is strongly affected by the noise.

The effect of such noise can be reduced if the calculation is made based on the amount of light measured over a sufficiently longer period before and after the timing of the luminance peak value, not limiting the period before and after that to two frames. The method for accomplishing this will be described with reference to FIG. 8.

As shown in FIG. 8, the processing circuit 10 consists of a subtractor 121, a steady-state light data memory 122, a first arithmetic device 123, a second arithmetic device 124, and a divider 125.

Image data Xi output from the imaging apparatus 12 is input to the subtractor 121, where unwanted steady-state light components, other than the projected light, are removed, and the resulting data is supplied to the first and second arithmetic devices 123 and 124.

The first arithmetic device 123 finds the product Xi·I, i.e., the product of the image data Xi and the timing or frame number I at which the image data Xi is output, for each pixel of the imaging device 71, and computes the sum $\Sigma Xi \cdot i$ over the entire frame. The second arithmetic device 124 computes $\Sigma Xi$, i.e., the sum of the image data Xi over the entire frame. Then, the divider 125 computes the temporal centroid, $\Sigma(Xi \cdot i)/\Sigma Xi$, of the image data Xi. The method of this computation is described in detail in Japanese Patent Unexamined Publication No. 8-308106 disclosed by applicant.

According to the three dimensional information measurement apparatus 1 of the above embodiment, the three dimensional information around the entire circumference of the object OB placed in a space inside the imaging mirror can be measured. In particular, since the entire circumference of the object OB is reflected at once in the imaging mirror 11, the three dimensional information can be measured in a one-shot operation without having to move the imaging apparatus 12 or the object OB. Therefore, there is no need to provide a moving driving device as used in the prior art, and the three dimensional information can be measured and input using a relatively simple configuration. Since there are no discontinuities in the image OBZ obtained by the imaging apparatus 12, there is no need to perform complex processing such as image merging processing. Furthermore, since three dimensional information around the entire circumference can be measured in a simple one-shot operation or action, the three dimensional information of the object OB can be measured and input at high speed. Accordingly, even when the target is a living creature such as a human being or an animal, the measurement can be made quite easily without concern that the target may move during measuring.

In the above embodiment, the reference light projection apparatus 13 has been described as projecting reference light in the form of a beam, but as the reference light projection apparatus 13 it is also possible to use an apparatus of the type that projects radiating reference light (annular reference light) and deflects this radiating reference light in the direction parallel to the axis J. In that case, since there is no need to rotate the reference light projection apparatus 13 about the axis J, the configuration can be further simplified.

The three dimensional information measurement apparatus 1 of the above embodiment has been described as using the imaging mirror 11 that is formed in the shape of an inverted truncated cone with a hollow interior, but it is also possible to use imaging mirrors whose cross sections cut along a vertical plane describe various curves such as a parabola, ellipse, semi-circle, etc. Three dimensional information around the entire circumference of the object OB placed inside the imaging mirror 11 can be input, but it will be appreciated that the invention is also applicable if the imaging mirror 11 is not formed in the shape of a complete ring but is formed with a limited field of view, for example, 180 degrees or 270 degrees. In this case also, the three dimensional information of the object OB can be measured at high speed from multiple viewpoints around its circumference. In this case, unnecessary portions of the reference light beam or reference light in the main scanning range can be omitted. As for the rotator type mirror, a large number of narrow rectangular plane mirrors may be arranged in the circumferential direction to approximate the shape of the rotating body. This serves to facilitate the fabrication of the rotator type mirror.

In the above embodiment, the optical mechanism and the three dimensional information computing section PR or processing circuit PR1, 2 may be assembled in the same housing or assembled respectively in separate housings. It is also possible to use a personal computer or the like as the whole or part of the three dimensional information computing section PR or processing circuit PR1, 2. Further, the structure, shape, and disposition of the three dimensional information measurement apparatus 1 itself or of each individual component thereof, and the circuit configuration of the processing circuit PR1, PR2 and its processing details, etc. can be modified or changed as necessary without departing from the spirit and scope of the present invention.

What is claimed is:

1. A three dimensional information measurement method for measuring three dimensional information on a target placed in an interior space of a rotator type mirror by using said rotator type mirror in combination with an imaging apparatus disposed with its light receiving axis aligned with a center axis of said rotator type mirror, comprising:

projecting reference light toward said rotator type mirror from a position on said center axis;

scanning said target with mirror reflected reference light that is produced by reflecting said reference light on said rotator type mirror; and obtaining the three dimensional information of said target, based on a physical quantity corresponding to the projection angle of said reference light and on a physical quantity corresponding to the position of a projected image obtained when said mirror reflected reference light that scanned said target is captured by said imaging apparatus via said rotator type mirror.

2. The three dimensional information measurement method according to claim 1, wherein said physical quantity corresponding to the projection angle is one selected from the group consisting of the projection angle, and elapsed time from the start of a subscan, and an amount of movement of a reference light projection and scanning apparatus.

3. The three dimensional information measurement method according to claim 1, wherein said physical quantity corresponding to the position of the projection image is one selected from the group consisting of a distance of the position of a projected image from a reference position, coordinates of a pixel on which the projected image is projected, and a direction opposing the pixel on which the projected image is projected.

4. The three dimensional information measurement method of claim 1, wherein said three dimensional information is of an entire circumference of said target.

5. A three dimensional information measurement apparatus for measuring three dimensional information on a target, comprising:

a rotator type mirror defining an interior space in which said target is placed;

an imaging apparatus disposed with its light receiving axis aligned with a center axis of said rotator type mirror;

a reference light projection and scanning apparatus including a motor rotating at least part of reference light projection and scanning apparatus to deflect light in a circumferential direction of said rotator type mirror and a scanner to deflect light in a direction parallel to said center axis of said rotator type mirror; and a computer receiving signals from said imaging apparatus and, based on a physical quantity corresponding to the projection angle of said reference light and on a physical quantity corresponding to the position of a projected image obtained from mirror reflected reference light detected by said imaging apparatus via said rotator type mirror, computes three dimensional information about said object.

6. The three dimensional information measurement apparatus according to claim 5, wherein said reference light projection and scanning apparatus is positioned within a cylindrical region near the center of a field of view of said imaging apparatus where said rotator type mirror does not exist when seen from the imaging apparatus.

7. The three dimensional information measurement apparatus according to claim 5, wherein said reference light projection and scanning apparatus includes gears.

8. The three dimensional information measurement apparatus according to claim 5, wherein said reference light projection and scanning apparatus includes a galvanometer scanner.

9. The three dimensional information measurement apparatus according to claim 5, wherein said computer is a personal computer.

10. The three dimensional information measurement apparatus according to claim 5 wherein said physical quantity correspond to the projection angle is one selected from the group consisting of the projection angle itself, and elapsed time from the start of the scanning apparatus and an amount of movement of said reference light projection and scanning apparatus.

11. A three dimensional information measurement apparatus according to claim 5 wherein said physical quantity corresponding to the position of the projection image is one selected from the group consisting of a distance of the position of a projected image from a reference position, coordinates of a pixel on which the projected image is projected, and a direction opposing the pixel on which the projected image is projected.

12. The three dimensional information measurement apparatus according to claim 5, wherein said three dimensional information is of an entire circumference of said target.

13. A three dimensional information measurement apparatus for measuring three dimensional information on a target placed in an interior space of a rotator type mirror by using said rotator type mirror in combination with an imaging apparatus disposed with its light receiving axis aligned with a center axis of said rotator type mirror, comprising:

reference light projection means for projecting reference light toward said rotator type mirror from a position on said center axis;

main scanning means for deflecting said reference light so that mirror reflected reference light, produced by reflecting said reference light on said rotator type mirror, scans said target around the circumference thereof;

sub scanning means for deflecting the projection angle of said reference light so that said mirror reflected reference light scans said target in a direction parallel to said center axis; and three dimensional information computing means for obtaining the three dimensional information of said target, based on a physical quantity corresponding to the projection angle of said reference light and on a physical quantity corresponding to the position of a projected image obtained when said mirror reflected reference light that scanned said target is captured by said imaging apparatus via said rotator type mirror.

14. The three dimensional information measurement apparatus according to claim 13, wherein said reference light projection means is positioned within a cylindrical region near the center of a field of view of said imaging apparatus where said rotator type mirror does not exist when seen from the imaging apparatus.

15. The three dimensional information measurement apparatus according to claim 13, wherein said main scanning means rotates said reference light projection means.

16. The three dimensional information measurement apparatus according to claim 13, wherein said main scanning means rotates part of said reference light projection means.

17. The three dimensional information measurement apparatus according to claim 13, wherein said sub scanning means includes a galvanometer scanner.

18. The three dimensional information measurement apparatus according to claim 13 wherein said three dimensional information computing means includes a personal computer.

19. The three dimensional information measurement apparatus according to claim 13 wherein said physical quantity corresponding to the projection angle is one selected from the group consisting of the projection angle itself, an elapsed time from the start of said subscanning means, an amount of movement of said main scanning means.

20. The three dimensional information measurement apparatus according to claim 13, wherein said physical quantity corresponding to the position of the projection image is one selected from the group consisting of a distance of the position of a projected image from a reference position, coordinates of a pixel on which the projected image is projected, and a direction opposing the pixel on which the projected image is projected.

21. The three dimensional information measurement apparatus according to claim 13, wherein said three dimensional information is of an entire circumference of said target.

22. A three dimensional information measurement apparatus for measuring three dimensional information on a target, comprising:
- a mirror having mirror surface facing to a space in which the target is placed;
- a reference light projection apparatus for projecting reference light to the target placed in the space via reflection of the mirror surface;
- an imaging apparatus for imaging the reference light on the target via reflection of the mirror surface; and
- a processor for generating a three dimensional information of a portion of the target on where the reference light is projected.

23. A three dimensional information measurement apparatus according to claim 22, further comprising:
- a scanning mechanism for moving the reference light on the target, wherein
- the imaging apparatus repeatedly images the reference light based on the movement of the reference light.

24. A three dimensional information measurement apparatus according to claim 22, wherein the mirror remains stationary relative to the target while one of the reference light and mirror moves relative to the other.

* * * * *